(12) United States Patent
Seok et al.

(10) Patent No.: US 11,407,999 B2
(45) Date of Patent: Aug. 9, 2022

(54) PHARMACEUTICAL COMPOSITION FOR PREVENTING OR TREATING ANGIOGENESIS RELATING OCULAR DISEASES COMPRISING INHIBITORS OF MCT EXPRESSION OR ACTIVITY

(71) Applicants: Seoul National University R&DB Foundation, Seoul (KR); AJOU UNIVERSITY INDUSTRY-ACADEMIC COOPERATION FOUNDATION, Suwon-si (KR)

(72) Inventors: Seung Hyeok Seok, Seoul (KR); Juha Song, Bucheon-si (KR); Ki Hwang Lee, Seoul (KR)

(73) Assignees: SEOUL NATIONAL UNIVERSITY R&DB FOUNDATION, Seoul (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/918,039

(22) Filed: Jul. 1, 2020

(65) Prior Publication Data
US 2021/0002637 A1 Jan. 7, 2021

(30) Foreign Application Priority Data
Jul. 1, 2019 (KR) .......................... 10-2019-0078999

(51) Int. Cl.
*A61K 31/5025* (2006.01)
*A61K 45/06* (2006.01)
*A61K 9/00* (2006.01)
*C12N 15/113* (2010.01)

(52) U.S. Cl.
CPC ........ *C12N 15/113* (2013.01); *A61K 31/5025* (2013.01); *A61K 9/0019* (2013.01); *A61K 45/06* (2013.01)

(58) Field of Classification Search
CPC .................................................... A61K 31/381
See application file for complete search history.

(56) References Cited

FOREIGN PATENT DOCUMENTS

| KR | 10-2014-0141818 | 12/2014 | |
|---|---|---|---|
| WO | WO-2006071897 A2 * | 7/2006 | ........... A61K 31/445 |

OTHER PUBLICATIONS

Guile (Bioorganic and Medicinal Chemistry Letters vol. 16 pp. 2260-2265. Published 2006). (Year: 2006).*
Fang (Molecular Pharmacology vol. 70 pp. 2108-2115 published 2006) (Year: 2006).*

(Continued)

*Primary Examiner* — Theodore R. Howell
*Assistant Examiner* — George W Kosturko
(74) *Attorney, Agent, or Firm* — Lex IP Meister, PLLC

(57) ABSTRACT

The present invention relates to a pharmaceutical composition for preventing or treating an angiogenesis-related ocular disease comprising an inhibitor of MCT expression or MCT activity as an active ingredient, and it can effectively prevent or treat an angiogenesis-related ocular disease without affecting the normal function of VEGF required for maintaining homeostasis of choriocapillary and visual cells, by specifically inhibiting only VEGF secreted by macrophages, different from conventional treatment.

7 Claims, 17 Drawing Sheets

Specification includes a Sequence Listing.

(56) References Cited

OTHER PUBLICATIONS

Song (IOVS vol. 59 pp. 3747-3754. Published online Jul. 2018). (Year: 2018).*

Jhudit Pérez-Escuredo et al., "Monocarboxylate transporters in the brain and in cancer", Biochimica et Biophysica Acta, 1863, pp. 2481-2497, Mar. 16, 2016.

Pascale Fisel et al., "Clinical and Functional Relevance of the Monocarboxylate Transporter Family in Disease Pathophysiology and Drug Therapy", Clin. Transl Sci., 11, 352-364, Apr. 16, 2018.

Christopher J. Layton et al., "Monocarboxylate Transporter Expression Remains Unchanged during the Development of Diabetic Retinal Neuropathy in the Rat", Investigative Ophthalmology & Visual Science, 46(8), 2878-2885, Aug. 2005.

Juha Song et al., "Lactic acid upregulates VEGF expression in macrophages and endothelial cells, facilitating choroidal neovascularization", section 45, Society for Leukocyte Biology 50th Annual Meeting, Oct. 5, 2017. (abstract only).

Juha Song et al., "Lactic Acid Upregulates VEGF Expression in Macrophages and Facilitates Choroidal Neovascularization", Investigative Ophthalmology & Visual Science, vol. 59, No. 8, pp. 3747-3754, Jul. 2, 2016.

* cited by examiner

[FIG. 1]
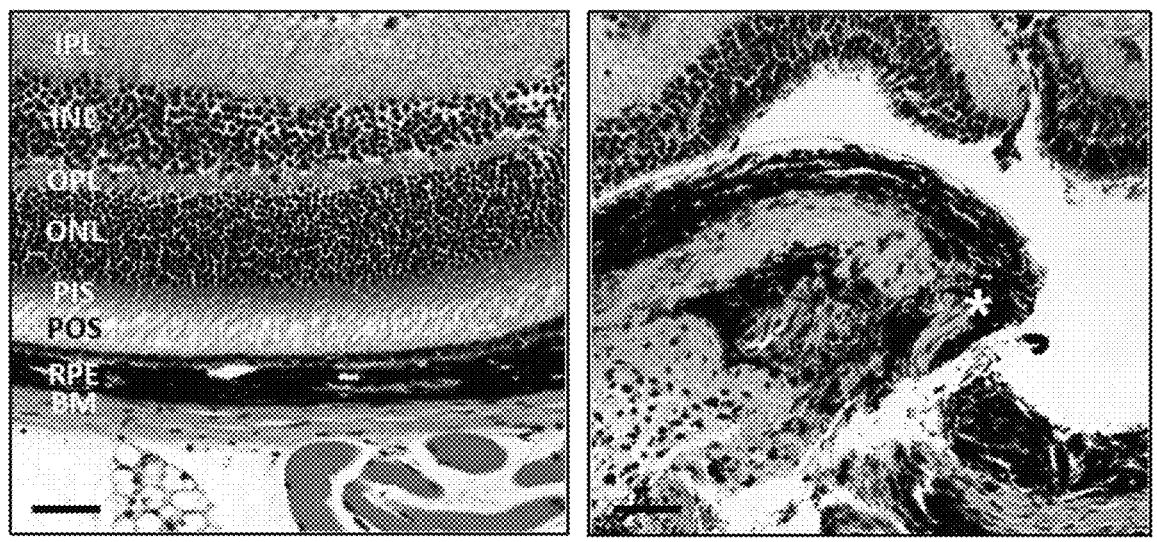
[FIG. 2]
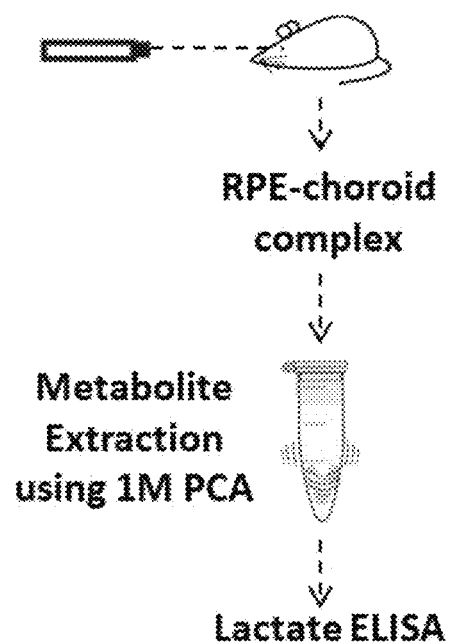

[FIG. 3]
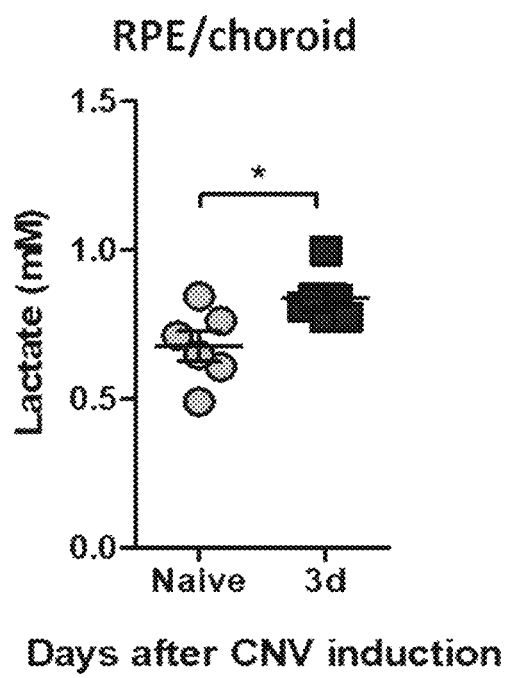
[FIG. 4a]
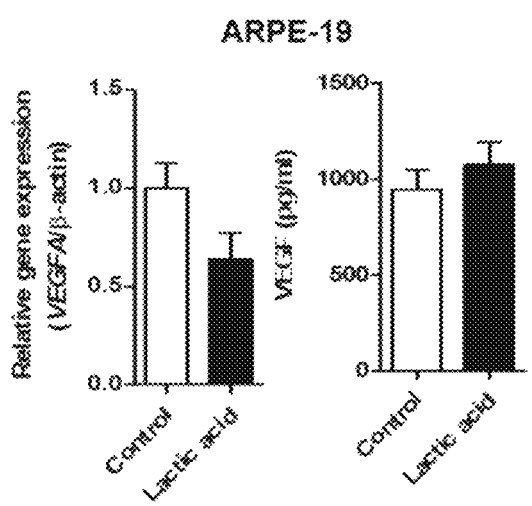

[FIG. 4b]
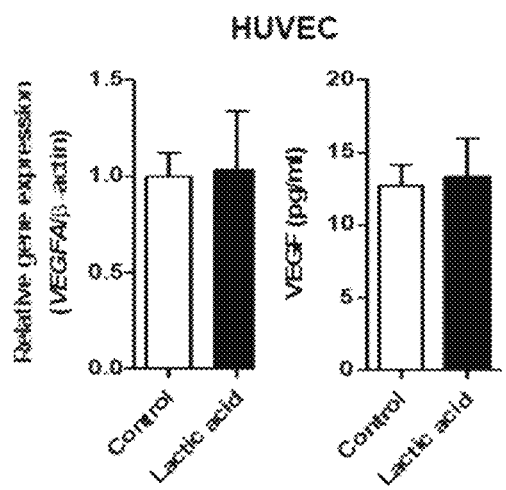
[FIG. 4c]
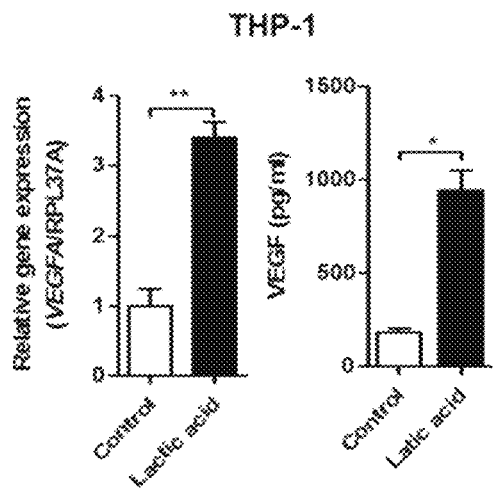

[FIG. 5]
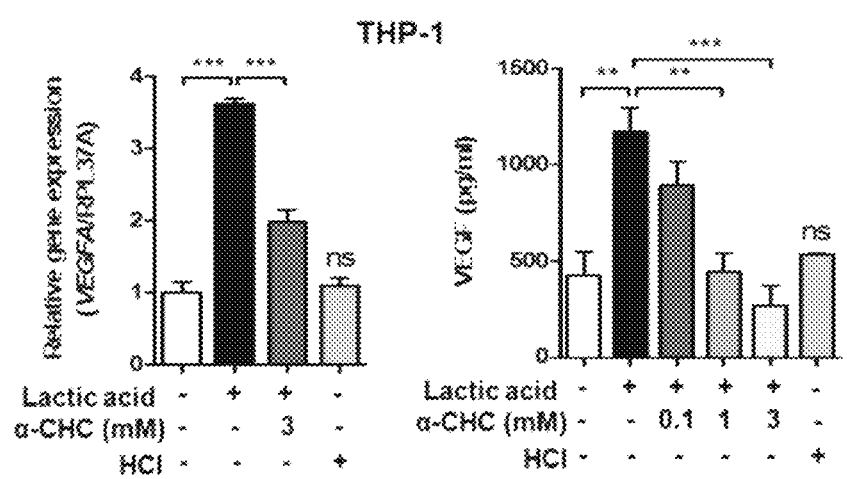
[FIG. 6a]
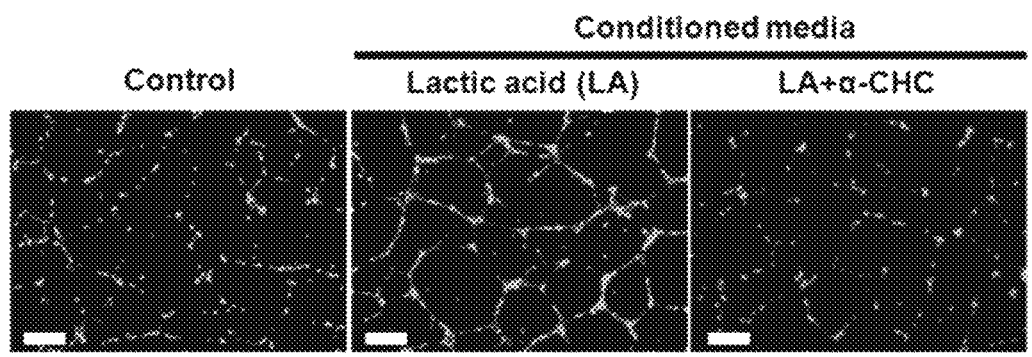

[FIG. 6b]
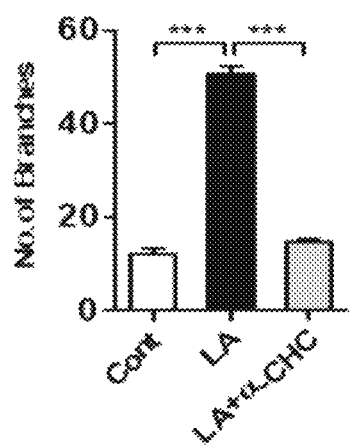

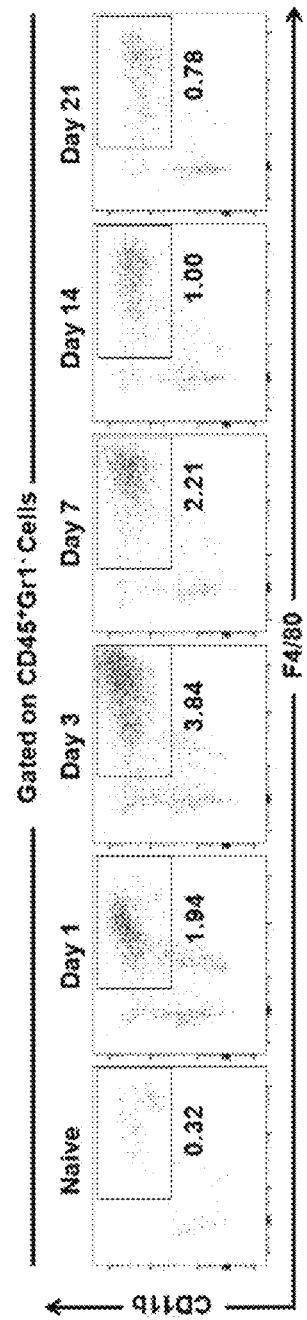
[FIG. 7a]

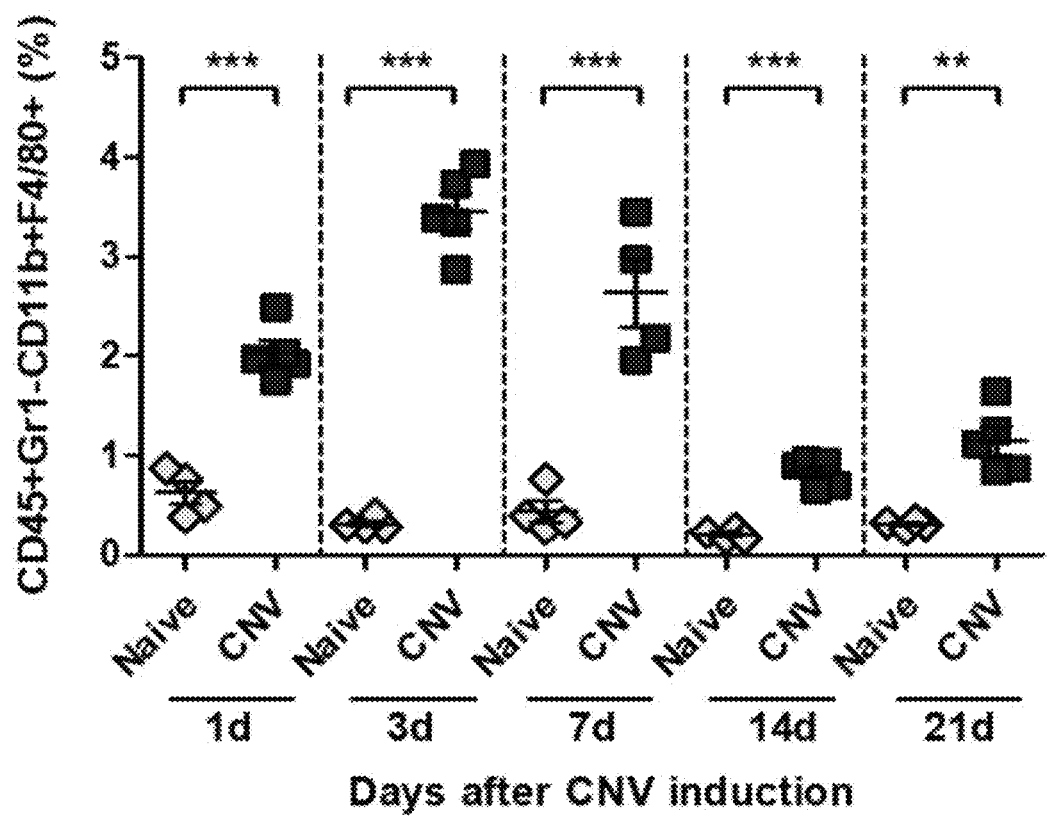
[FIG. 7b]

[FIG. 7c]
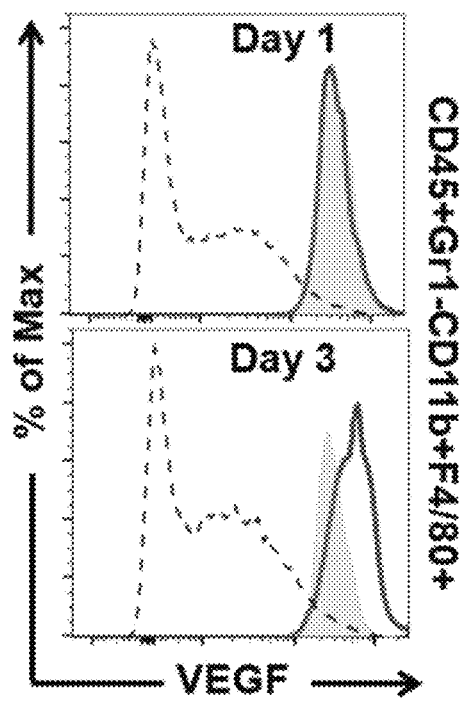

[FIG. 7d]
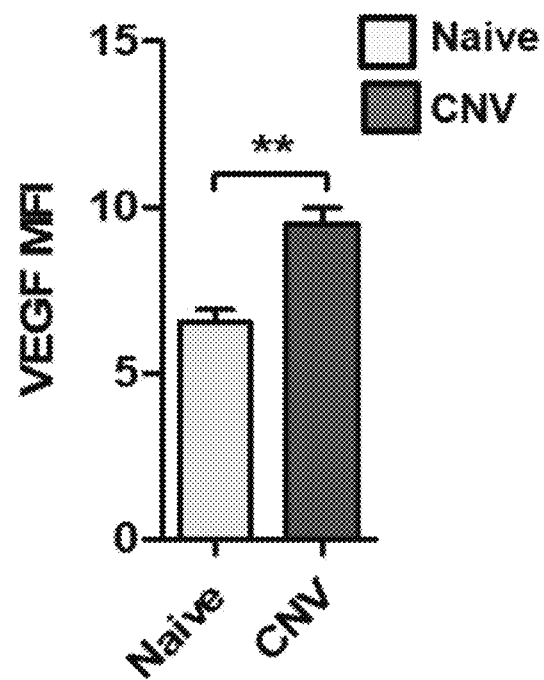
[FIG. 8a]
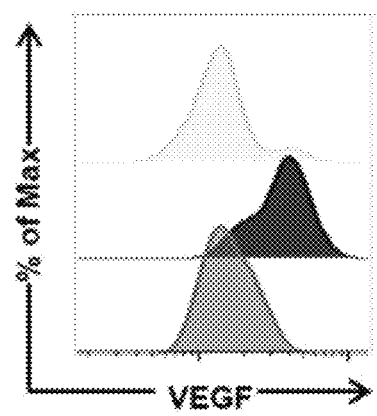

[FIG. 8b]
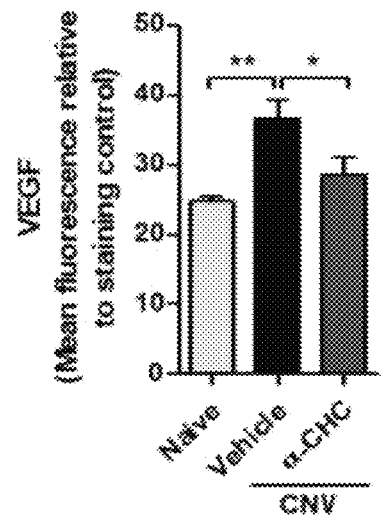
[FIG. 8c]
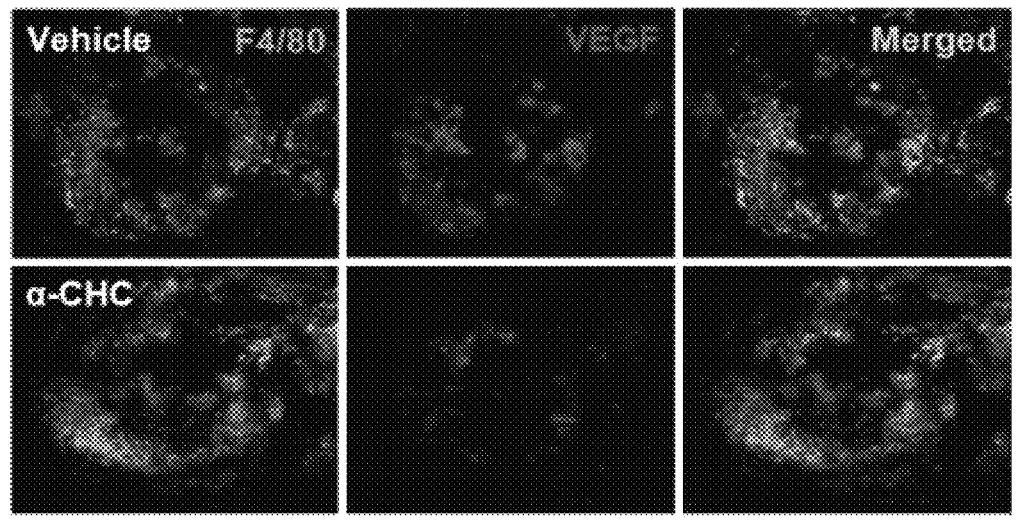

[FIG. 8d]
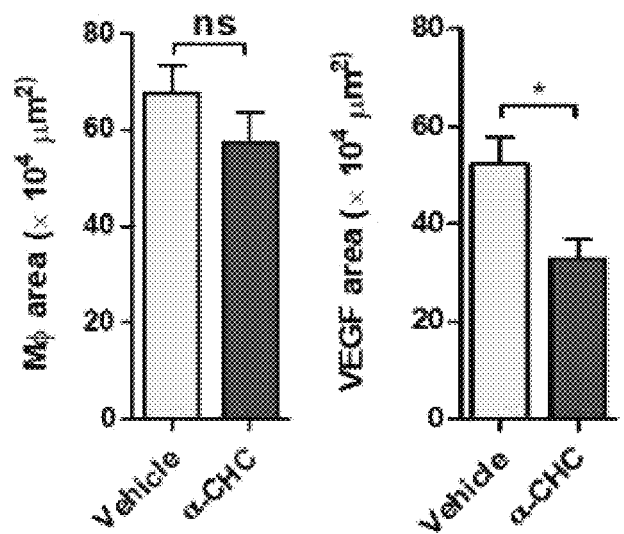
[FIG. 8e]
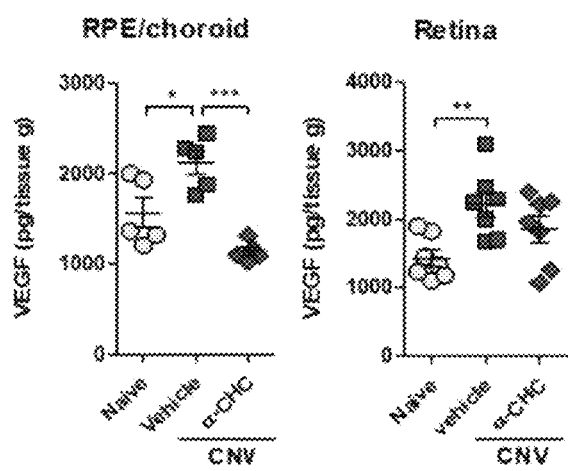

[FIG. 8f]
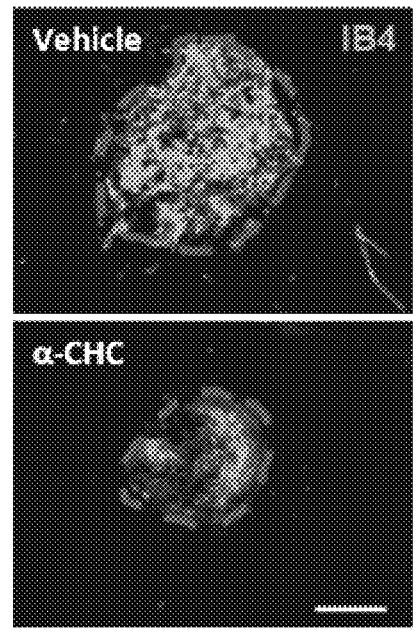
[FIG. 8g]
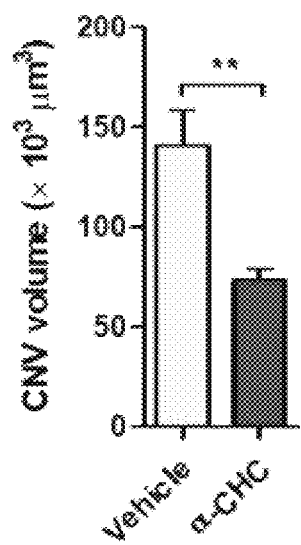

[FIG. 9a]
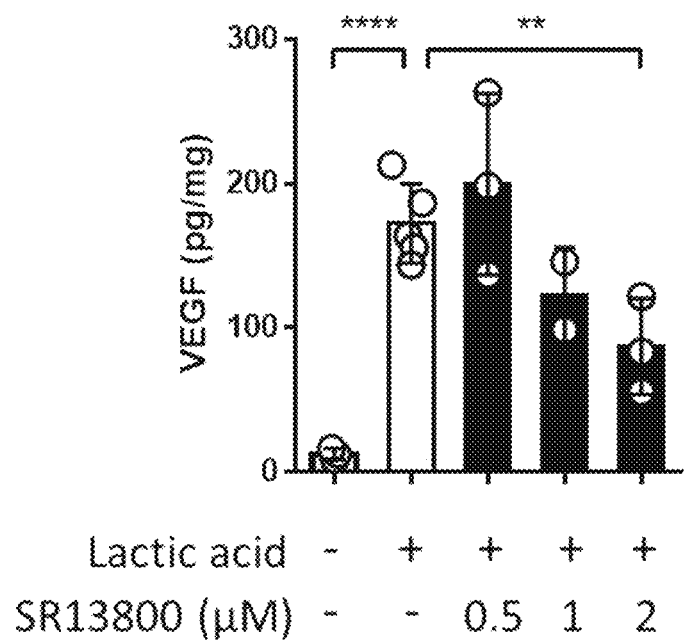
[FIG. 9b]
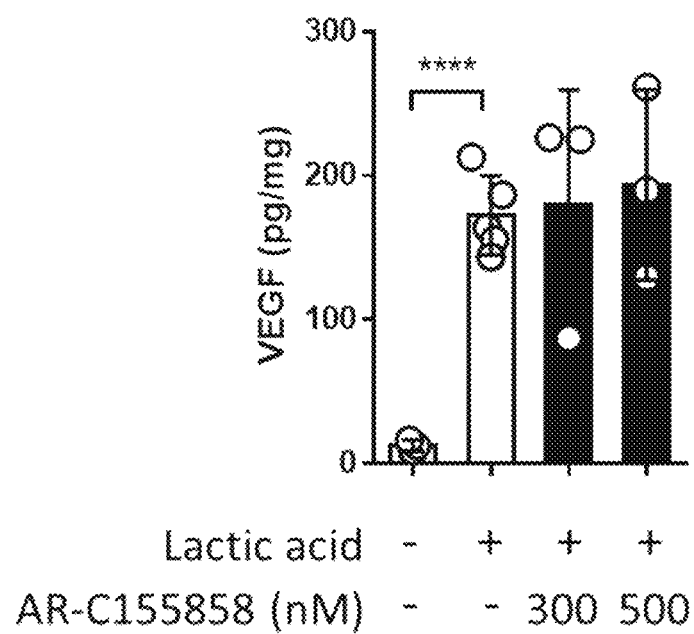

[FIG. 10a]
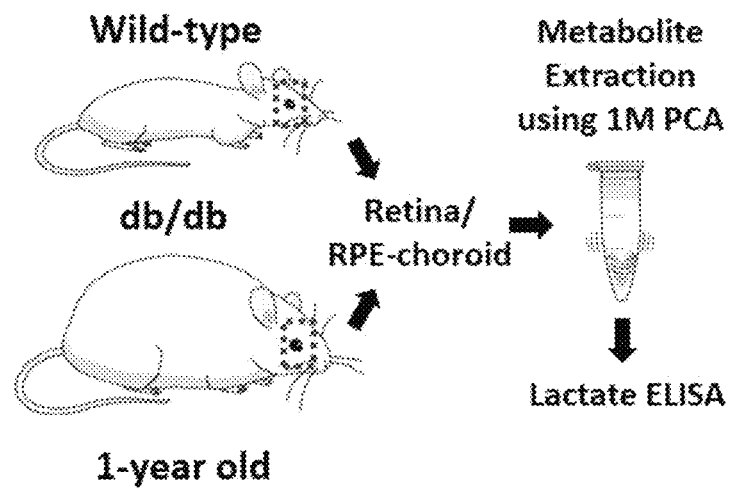
[FIG. 10b]
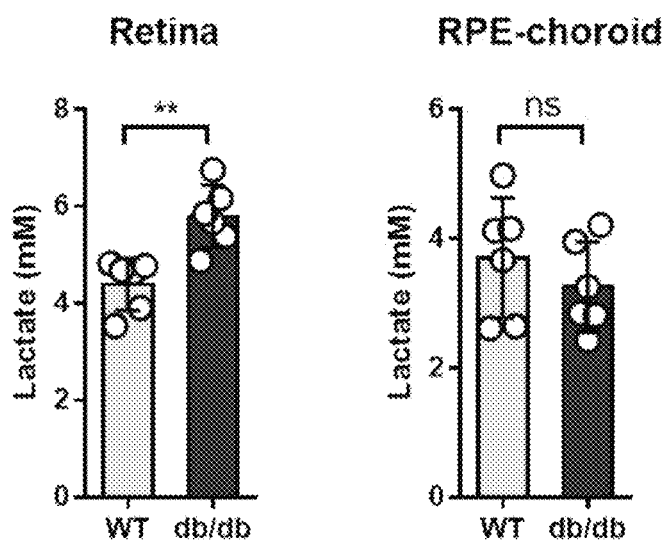

[FIG. 11a]
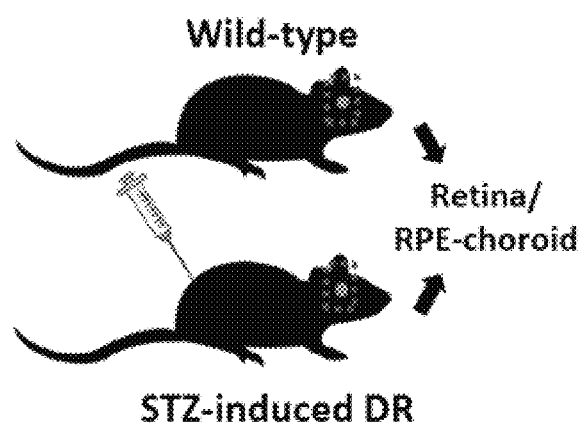
[FIG. 11b]
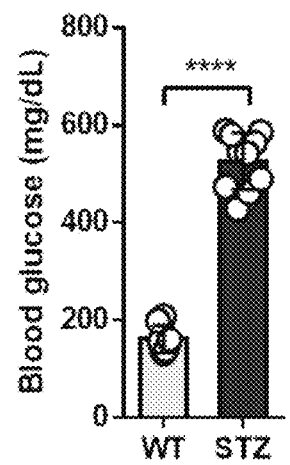

[FIG. 12]
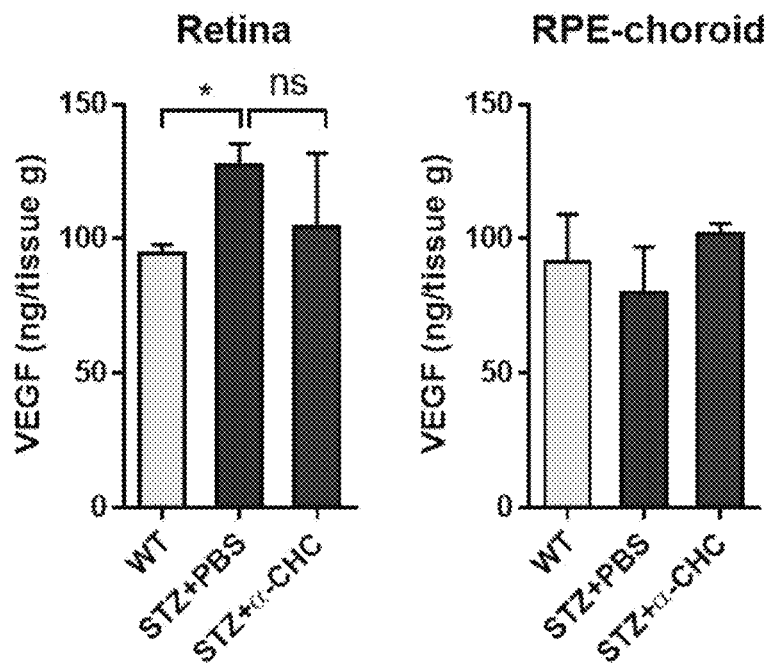
[FIG. 13]
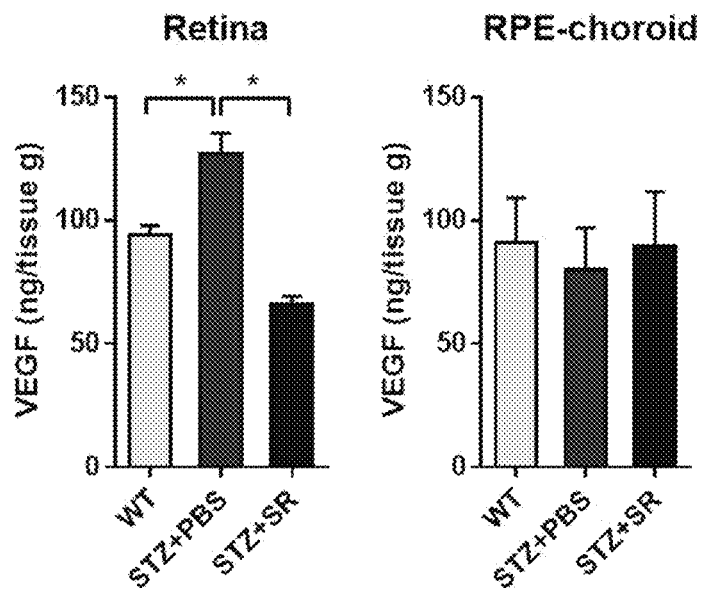

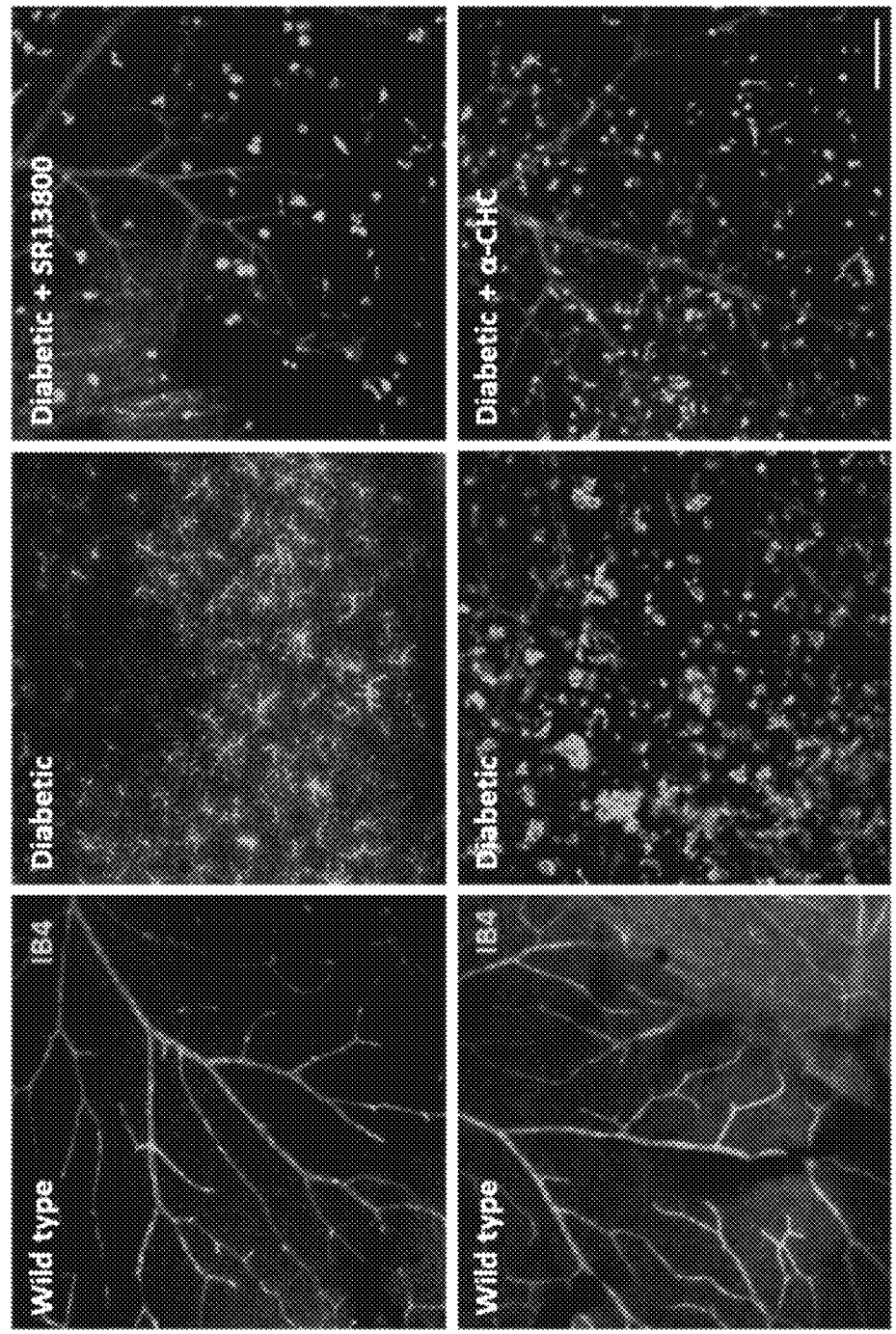
[FIG. 14]

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic_beta-actin_Forward

<400> SEQUENCE: 1
attgccgaca ggatgcagaa                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic_beta-actin_Reverse

<400> SEQUENCE: 2
gctgatccac atctgctgga a                                            21
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic_RPL37A_Forward

<400> SEQUENCE: 3
attgaaatca gccagcacgc                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetic_RPL37A_Reverse

<400> SEQUENCE: 4
aggaaccaca gtgccagatc c                                             21

<210> SEQ ID NO 5
<211> LENGTH: 20
<212> TYPE: DNA
<213> ORGANISM: Artificial Sequence
<220> FEATURE:
<223> OTHER INFORMATION: Synthetic_VEGFA_Forward

<400> SEQUENCE: 5
attgaaatca gccagcacgc                                               20

<210> SEQ ID NO 6
<211> LENGTH: 21
<212> TYPE: DNA
<213> ORGANISM: Artificial Sequence
<220> FEATURE:
<223> OTHER INFORMATION: Synthetic_VEGFA_Reverse

<400> SEQUENCE: 6
aggaaccaca gtgccagatc c                                             21
```

PHARMACEUTICAL COMPOSITION FOR PREVENTING OR TREATING ANGIOGENESIS RELATING OCULAR DISEASES COMPRISING INHIBITORS OF MCT EXPRESSION OR ACTIVITY

CROSS-REFERENCE TO RELATED APPLICATIONS

This application claims the benefit of Korea Patent Application No. 10-2019-0078999 filed on Jul. 1, 2019 with the Korea Industrial Property Office, the entire disclosure of which is hereby incorporated by reference.

BACKGROUND OF THE INVENTION

1. Field of the Invention

The present invention relates to a pharmaceutical composition for preventing or treating an angiogenesis-related ocular disease comprising an inhibitor of MCT expression or activity as an active ingredient.

2. Description of the Related Art

Diseases such as diabetic retinopathy, age-related macular degeneration, retinopathy of prematurity and angiogenic glaucoma are ocular diseases of which major cause is angiogenesis, and they are causing millions of blindness worldwide each year. Vascular endothelial growth factor (VEGF) is known to play the most important role among substances inducing angiogenesis, and induces angiogenesis as the amount of VEGF in retinal endothelial cells, retinal pigment epithelium cells and retinal pericytes is increased when ischemia occurs in eyes.

Therefore, conventional treatment of an angiogenesis-related ocular disease is mainly dominated by a method of directly injecting an antibody against a vascular endothelial growth factor (anti-VEGF) pathologically increased in eyes into eyes and degrading excessively produced blood vessels. Various anti-VEGF drugs have been developed and marketed to date, but conventional anti-VEGF drugs have a problem of excessively inhibiting even VEGF necessary for normal blood vessel maintenance and physiological action in retina and retinal pigment epithelium, and the like, and it is reported that it occurs side effects from systemic absorption and local complications of eyes (for example, rapid increase in blood pressure, stroke, myocardial infarction, death, endophthalmitis, tractional retinal detachment, uveitis, rhegmatogenous retinal detachment, etc.). Accordingly, there is a need to develop a new therapeutic agent for an angiogenesis-related ocular disease that does not interfere with normal immunovascular axis.

(Patent document 1) Korean Patent Publication No. 10-2014-0141818

SUMMARY OF THE INVENTION

An object of the present invention is to provide a pharmaceutical composition for preventing or treating an angiogenesis-related ocular disease, comprising an inhibitor which inhibits expression of an MCT (Monocarboxylate transporter) gene or activity of an MCT protein as an active ingredient.

Another object of the present invention is to provide a method of prevention and/or treatment of an angiogenesis-related ocular disease, comprising administering a pharmaceutically effective amount of an inhibitor which inhibits expression of an MCT gene or activity of an MCT protein to a subject in need of prevention and/or treatment of an angiogenesis-related ocular disease.

BRIEF DESCRIPTION OF THE DRAWINGS

FIG. 1 shows the result of H&E staining of the control without laser irradiation and the retinal tissue after laser irradiation. In FIG. 1, the left panel shows the retinal tissue of the control without laser irradiation, and the right panel shows the retinal tissue on day 1 after laser irradiation.

FIG. 2 is a schematic diagram showing the process of measuring the concentration of lactic acid in the RPE-choroid tissue of the CNV mouse.

FIG. 3 shows the concentration of lactic acid (mM) in the RPE-choroid tissue isolated from the control (naive) and the CNV mouse.

FIG. 4a to FIG. 4c show the VEGF expression patterns according to the treatment of lactic acid in retinal pigment epithelium cells (ARPE-19, FIG. 4a), endothelial cells (HUVEC, FIG. 4b), and infiltrated macrophages (THP-1, FIG. 4c).

FIG. 5 shows the VEGF expression when treating lactic acid to THP-1 cells under presence or absence of α-CHC.

In FIG. 4a to FIG. 4c and FIG. 5, the left graphs show the relative VEGFA mRNA expression, the right graphs show the VEGF protein expression, and control means the control without treating lactic acid.

FIG. 6a and FIG. 6b show the result of the tube formation assay which shows whether macrophages stimulated by lactic acid promote angiogenesis in HUVEC under presence or absence of CHC. Specifically, FIG. 6a shows the image of visualizing tube formation of endothelial cells with Calcein AM, and FIG. 6b shows the result of calculating the total number of branches using Image J software.

FIG. 7a to FIG. 7d show the result of performing flow cytometry to investigate infiltration of macrophages to CNV lesions and VEGF expression. Specifically, FIG. 7a shows the result of performing flow cytometry for macrophage markers using cells isolated from the RPE-choroid tissue of the CNV mouse, and FIG. 7b shows the percentage (%) of the macrophages infiltrated in CNV mouse eyes over time after laser irradiation, and FIG. 7c shows representative histograms for VEGF in macrophages of the CNV mouse on Day 3 after laser irradiation, and FIG. 7d shows the result of quantifying the fluorescence intensity (MFI; mean fluorescence intensity) of VEGF in macrophages of the control (naive) and the CNV mouse.

FIG. 8a and FIG. 8b show the result of performing flow cytometry for VEGF after intravitreally injecting the MCT inhibitor (α-CHC) to the CNV mouse. Specifically, FIG. 8a shows a histogram, and FIG. 8b shows the concentration of VEGF as the relative mean fluorescence intensity compared to the staining control.

FIG. 8c and FIG. 8d show the result of performing immunohistostaining for F4/80 or VEGF on day 3 after injecting the MCT inhibitor (α-CHC) or PBS to the CNV mouse. Specifically, FIG. 8c is the image obtained by performing immunohistostaining for F4/80 or VEGF in the MCT inhibitor injecting group or vehicle group, and FIG. 8d shows quantified F4/80 (left graph) and VEGF (right graph) stained parts, respectively, using Image J software.

FIG. 8e shows the result of measuring the VEGF protein expression (secretion amount) (pg/tissue g) in RPE/choroid and retina regions of the vehicle group and MCT inhibitor injecting group.

FIG. 8f and FIG. 8g show the result of quantifying choroidal neovascularization (CNV) in the vehicle group and MCT inhibitor injecting group. Specifically, FIG. 8f is the confocal image obtained by performing immunohistostaining for IB4 (isolectin B4) in the vehicle group (top image) and MCT inhibitor injecting group (bottom image), and FIG. 8g shows the graph of quantifying IB4 positive signals. In FIG. 8f, the red dotted line indicates the region stained with IB4.

FIG. 9a shows the VEGF protein expression when lactic acid is treated to THP-1 cells under presence or absence of the MCT inhibitor (SR13800), and FIG. 9b shows the VEGF protein expression when lactic acid is treated to THP-1 cells under presence or absence of the MCT inhibitor (AR-C155858).

FIG. 10a shows a schematic diagram which shows the process of measuring lactic acid in the retina and RPE-choroid tissue in eyes of the wild type mouse (wild type) as a control and diabetic mouse (db/db mouse), and FIG. 10b shows the concentration (mM) of lactic acid measured in the retina and RPE-choroid tissue of the wild type mouse (WT) and diabetic mouse (db/db).

FIG. 11a is a schematic diagram showing the process of preparing a mouse in which diabetes is caused and diabetic retinopathy (DR) is induced by STZ, and FIG. 11b shows the result (mg/dL) of measuring the blood glucose in the blood of the mouse (STZ) in which diabetes and diabetic retinopathy are caused by STZ and the wild type mouse (WT).

FIG. 12 shows graphs of measuring the VEGF protein secretion amount (ng/tissue g) of the RPE-choroid tissue and the retina by injection of PBS (vehicle group) and α-CHC (α-CHC administration group) in eyes. In FIG. 12, STZ means the mouse in which diabetic retinopathy is caused, and WT means a normal group that is the wild type mouse, and ns means that it is not statistically significant.

FIG. 13 shows graphs of measuring the VEGF protein expression of the retina and RPE-choroid tissue by injection of PBS (vehicle group) and SR13800 (SR13800 administration group) in eyes. In FIG. 12, STZ means the mouse in which diabetic retinopathy is caused, and WT means a normal group that is the wild type mouse, and SR means SR13800 administration.

FIG. 14 is pictures of photographing changes of angiogenesis and retinal vascular hemorrhage in the STZ mouse by injection of the vehicle group, α-CHC administration group, and SR13800 administration group in eyes.

In the drawings, * means P<0.05, and  means P<0.01, and * means P<0.001, and **** means P<0.0001.

DETAILED DESCRIPTION

The present inventors have confirmed that an inhibitor (for example, SR13800) which inhibits expression of an MCT gene or activity of an MCT protein effectively inhibits VEGF expression and/or angiogenesis, thereby suggesting a use for prevention, treatment, and/or improvement of an angiogenesis-related ocular disease (for example, diabetic retinopathy) of an MCT protein and expression of an MCT gene.

One example provides a pharmaceutical composition for preventing or treating an angiogenesis-related ocular disease, comprising an inhibitor which inhibits expression of an MCT (Monocarboxylate transporter) gene or activity of an MCT protein as an active ingredient. Another example provides a method of prevention or treatment of an angiogenesis-related ocular disease comprising administering an inhibitor (or a composition comprising the inhibitor) which inhibits expression of an MCT (Monocarboxylate transporter) gene or activity of an MCT protein to a subject. In one example, the method of prevention or treatment of an angiogenesis-related ocular disease may further comprise confirming (selecting) a subject in need of prevention and/or treatment of an angiogenesis-related ocular disease, before administering an inhibitor which inhibits expression of an MCT gene or activity of an MCT protein.

According to one example, the MCT gene may be at least one selected from the group consisting of MCT1, MCT2, AIM, and MCT4.

According to one example, the MCT gene may be at least one selected from the group consisting of MCT1 (SLC16A1), MCT2(SLC16A7), MCT3(SLC16A8), and MCT4(SLC16A3).

According to one example, the MCT protein may be at least one selected from the group consisting of MCT1, MCT2, MCT3, and MCT4.

According to one example, MCT may be at least one selected from the group consisting of MCT1 (Monocarboxylate transporter 1: e.g., human MCT1 (gene: GenBank Accession Nos. NM_001166496.1, NM_003051.3, etc.; protein: GenBank Accession Nos. NP_001159968.1, NP_003042.3, etc.), mouse MCT1 (gene: GenBank Accession Nos. NM_009196.4, etc.; protein: GenBank Accession Nos. NP_033222.1, etc.)), MCT2 (Monocarboxylate transporter 2: e.g., human MCT2 (gene: GenBank Accession Nos. NM_001270622.2, NM_001270623.2, NM_004731.5, etc.; protein: GenBank Accession Nos. NP_001257551.1, NP_001257552.1, NP_004722.2, etc.), mouse MCT2 (gene: GenBank Accession Nos. NM_011391.2, NM_001358496.1, NM_001358915.1, etc.; protein: GenBank Accession Nos. NP_035521.1, NP_001345425.1, NP_001345844.1, etc.)), MCT3 (Monocarboxylate transporter 3: e.g., human MCT3 (gene: GenBank Accession Nos. NM_013356.2, etc.; protein: GenBank Accession Nos. NP_037488.2, etc.), mouse MCT3 (gene: GenBank Accession Nos. NM_020516.2, etc.; protein: GenBank Accession Nos. NP_065262.1, etc.)), and MCT4 (Monocarboxylate transporter 4: e.g., human MCT4 (gene: GenBank Accession Nos. NM_001042422.2, NM_001042423.2, NM_001206950.1, NM_001206951.1, NM_001206952.1, etc.; protein: GenBank Accession Nos. NP_001035887.1, NP_001035888.1, NP_001193879.1, NP_001193880.1, NP_001193881.1, etc.), mouse MCT4 (gene: GenBank Accession Nos. NM_001038653.1, NM_001038654.1, NM_030696.3, etc.; protein: GenBank Accession Nos. NP_001033742.1, NP_001033743.1, NP_109621.1, etc.)).

MCT family consists of 14 subtypes, and MCT1, 2, 3 and 4 among subtypes of MCT promote proton-linked transport of monocarboxylate which is metabolically important such as lactate, pyruvate, and ketone bodies. It differs depending on tissue and species, but it is known that MCT1 or MCT2 mainly absorbs lactic acid for neogenesis of ketone bodies or glucose, and MCT3 is mainly expressed in retinal pigment epithelium, and MCT4 is mainly expressed in glycolytic cells.

According to one example, the composition (or inhibitor which inhibits expression of an MCT gene or activity of protein, hereinafter, MCT inhibitor) may selectively inhibit expression of MCT1 gene or activity of MCT1 protein among MCT, and minimize side effects such as inhibition of development or physiological action of a subject, and the like, when using the composition.

According to one example, in an angiogenesis-related ocular disease (for example, choroidal neovascularization, age-related macular degeneration, or diabetic retinopathy), expression of lactic acid (lactate) may be increased, and lactic acid may increase VEGF expression in macrophages, and the composition according to one example may reduce VEGF gene expression, VEGF protein expression and/or secretion, increased by lactic acid, thereby showing an excellent effect of preventing or treating an angiogenesis-related ocular disease. In one example, the lactic acid increased in the diseases may not increase VEGF expression in retinal pigment epithelium cells and/or endothelial cells, but may increase VEGF expression specifically in macrophages.

According to one example, the composition (or MCT inhibitor) may inhibit absorption and/or secretion of lactic acid of macrophages.

According to one example, the composition (or MCT inhibitor) may inhibit VEGF (vascular endothelial growth factor) secretion in macrophages.

According to one example, the composition (or MCT inhibitor) specifically inhibits secretion of VEGF increasing abnormally in infiltrated macrophages and does not affect secretion of VEGF required for normal blood vessel maintenance and physiological action, and therefore it may be used in use for prevention or treatment of an angiogenesis-related ocular disease without side effects.

The composition (or MCT inhibitor) according to one example may exhibit an effect of prevention or treatment of choroidal neovascularization and/or age-related macular degeneration by inhibiting VEGF secretion (or expression) in macrophages infiltrated in the retinal pigment epithelial (RPE) layer and choroid tissue in eyes.

The composition (or MCT inhibitor) according to one example may exhibit an effect of prevention or treatment of diabetic retinopathy by inhibiting VEGF secretion (or expression) in the retinal tissue in eyes, and specifically, it may exhibit an effect of prevention or treatment of diabetic retinopathy by inhibiting VEGF secretion (or expression) in macrophages infiltrated in the retinal tissue.

According to one example, the inhibitor may be at least one selected from the group consisting of siRNA (small interference RNA), shRNA (short hairpin RNA), miRNA (microRNA), ribozyme, DNAzyme, PNA (peptide nucleic acids), antisense oligonucleotide, antibody, aptamer, extract, and compound.

According to one example, the compound may be at least one selected from the group consisting of SR13800 (Cas No. 227321-12-2), AZD-3965 (Cas No. 1448671-31-5), AR-C15588 (Cas No. 496791-37-8), AR-C117977 (Cas No. 216685-07-3), 7ACC1 (DEAC, or Coumarin D 1421) (Cas No. 50995-74-9), 7ACC2 (DC7876) (Cas No. 1472624-85-3), α-CHC (α-cyano-4-hydroxycinnamate, α-Cyano-4-hydroxycinnamic Acid) (Cas No. 28166-41-8), pCMB (p-chloromercuribenzoic acid) (Cas No. 59-85-8), phloretin (Cas No. 60-82-2), quercetin (Cas No. 117-39-5), DIDS (4,4'-diisothiocyanostilbene-2,20-disulfonate) (Cas No. 207233-90-7), UK-5099 (Cas No. 56396-35-1), niflumic acid (Cas No. 4394-00-7), NPPB (5-nitro-2-(3-phenylpropylamino)-benzoate) (Cas No. 107254-86-4), GW604714X, GW450863X, luteolin (Cas No. 491-70-3), and lonidamine (Cas No. 50264-69-2).

According to one example, the compound with low potency and specificity acts various kinds of MCT subtypes, and therefore side effects may occur in normal development or physiological action.

According to one example, at least one compound selected from the group consisting of AZD-3965, and SR13800 may effectively treat an angiogenesis-related ocular disease without side effects in normal development or physiological action, by selectively inhibiting activity of MCT1.

The AZD-3965 may have the general formula of the following chemical formula 1, and the SR13800 may have the general formula of the following chemical formula 2.

[Chemical formula 1]

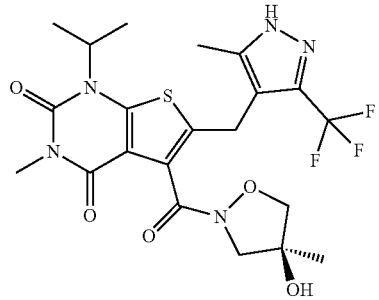

[Chemical formula 2]

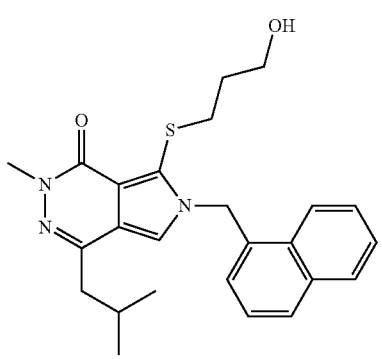

According to one example, in an angiogenesis-related ocular disease (for example, choroidal neovascularization, age-related macular degeneration, or diabetic retinopathy), expression of lactic acid (lactate) may be increased, and the composition according to one example may reduce VEGF gene expression, VEGF protein expression and/or secretion, increased by lactic acid, thereby exhibiting an excellent effect of preventing or treating an angiogenesis-related ocular disease.

According to one example, at least one compound selected from the group consisting of AZD-3965, and SR13800 may have a more excellent effect of prevention or treatment of an angiogenesis-related ocular disease than α-CHC.

According to one specific example, at least one compound selected from the group consisting of AZD-3965, and SR13800 may have a more excellent effect of prevention or treatment of diabetic retinopathy than α-CHC.

Herein, "diabetic retinopathy (DR)" means a complication in which peripheral circulation disorder occurs due to diabetes and then, microcirculation of the retina is impaired, resulting in decreased vision, and may include proliferative DR (PDR), non-proliferative DR (NPDR) and DR at high altitude.

According to one example, at least one compound selected from the group consisting of AZD-3965, and SR13800 may have at least one excellent effect selected from the group consisting of the following (1) to (3) than α-CHC, even though it is administered at a lower concentration than α-CHC:

(1) inhibition of VEGF expression increased by high blood glucose in retinal tissue;

(2) inhibition of angiogenesis occurring by high blood glucose in retinal tissue; and (3) specific inhibition of expression of the MCT1 gene and/or activity of MCT1, resulting in low side effects in normal development or physiological action.

According to one example, at least one compound selected from the group consisting of AZD-3965, and SR13800 may not affect normal function of VEGF required for maintenance of homeostasis of visual cells, and for example, it may effectively inhibit VEGF expression and/or angiogenesis of retinal tissue occurring in diabetic retinopathy, but may not affect VEGF expression of the retinal pigment epithelial (RPE) layer and choroid tissue.

According to one example, at least one compound selected from the group consisting of AZD-3965, and SR13800 may have a more excellent effect of inhibition of VEGF secretion in macrophages infiltrated in the retinal pigment epithelial (RPE) layer and choroid tissue in eyes than α-CHC.

According to one example, it may comprise the compound or its pharmaceutically acceptable salt.

Herein, "pharmaceutically acceptable salt" means a salt in a form which can be pharmaceutically used among salts that are substances that cations and anions are bound by electrostatic attraction, and commonly, it may be a metal salt, salt with organic base, salt with inorganic acid, salt with organic acid, salt with basic or acidic amino acid, and the like. For example, it may be an alkali metal salt (sodium salt, potassium salt, etc.), alkali earth metal salt (calcium salt, magnesium salt, barium salt, etc.), aluminum salt, or the like, as the metal salt; and it may be a salt with triethylamine, pyridine, picoline, 2,6-lutidine, ethanol amine, diethanol amine, triethanol amine, cyclohexyl amine, dicyclohexyl amine, N,N-dibenzylethylene diamine, or the like, as the salt with organic salt; and it may be a salt with chloric acid, hydrobromic acid, nitric acid, sulfuric acid, phosphoric acid, or the like, as the salt with inorganic acid; and it may be a salt with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, or the like as the salt with organic acid; and it may be a salt with arginine, lysine, ornithine, or the like, as the salt with basic amino acid; and it may be a salt with aspartic acid, glutamic acid, or the like, as the salt with acidic amino acid.

According to one example, the angiogenesis-related ocular disease may be at least one selected from the group consisting of age-related macular degeneration (AMD), diabetic retinopathy, diabetic macular edema, choroidal neovascularization, angiogenic glaucoma, corneal vascularization, central retinal vein occlusion, branch retinal vein occlusion, proliferative vitreoretinopathy, pigmental retinopathy, ischemic optic neuropathy, retinopathy of prematurity, epidemic keratoconjunctivitis, angiogenic iris disease, retrolental fibroplasia, atopic keratitis, superior limbic keratitis, pterygium, and phlyctenular keratoconjunctivitis.

According to one example, at least one compound selected from the group consisting of AZD-3965, and SR13800 may be effective specifically in prevention or treatment of diabetic retinopathy among the angiogenesis-related ocular disease than α-CHC.

According to one example, the composition may be formulated by further comprising at least one pharmaceutically acceptable carrier, excipient or diluent in addition to the active ingredient. For example, the pharmaceutically acceptable carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, metalhydroxybenzoate, propylhydroxybenzoate, talc, magnesium stearate or mineral oil, ore the like. In addition, a diluent, dispersing agent, surfactant, solvent, disintegrating agent, sweetener, binding agent, covering material, inflating agent, lubricant, glydent, or flavoring agent may be additionally added.

According to one example, the composition (or MCT inhibitor) may be formulated in a formulation suitable for administration, together with a pharmaceutically acceptable additive, in some cases.

According to one example, the composition may be at least one formulation selected from the group consisting of eye drop, eye ointment, injection, eye intercalator, granule, tablet, pill, capsule, gel, syrup, suspension, emulsion, drip, and liquid. In the injection, a conventional additive such as a solvent, tonicifying agent, suspending agent, emulsifier, stabilizer, preservative, or the like, may be comprised.

The formulation suitable for oral administration includes tablets, granules, syrup and powder, and the like; and the formulation suitable for parenteral administration includes injection, eye drop, eye ointment, adhesive preparation, gel and eye intercalator. These formulations may be prepared using general technology widely used in the corresponding field. In addition, the composition of the present invention may be formulated as a formulation for intraocular implants or formulation prepared as DDS (Drug delivery System) such as microspheres, and the like, in addition to these formulations.

According to one example, the composition may be administered by any known delivery system and/or administration route.

The subject to which an effective dose of the composition or active ingredient (MCT inhibitor) is administered may be a mammal including human, dog, cat, horse, pig, goat, rabbit, mouse, rat, and the like, or a cell, tissue or its culture, or the like isolated therefrom.

Herein, "administration" means introducing the composition or active ingredient (MCT inhibitor) to a subject by any appropriate method, and as the administration route, it may be administered through various oral or parenteral routes capable of reaching target tissue. The administration method may be all the routes commonly used, and for example, it may be oral administration or parenteral administration such as intravenous administration, intramuscular administration, subcutaneous administration, intraperitoneal administration and lesion site topical administration. In one example, the administration route of the composition (or MCT inhibitor) may be selected from the group consisting of intravitreal administration, intraconjunctival administration, subconjunctival administration, and subtenon administration.

According to one example, the composition is administered in a pharmaceutically effective dose. Herein, 'pharmaceutically effective dose' means an amount sufficient for treating diseases at a reasonable benefit/risk ratio applicable to medical treatment, and the effective dose level may be determined according to factors including the kind of patient's disease, severity, drug activity, sensitivity to the drug, administration time, administration route and excretion rate, treatment period, drug concurrently used, and other factors well known in the medical field.

According to one example, the composition (or MCT inhibitor) may be administered as an individual therapeutic agent, or administered in combination with other angiogenesis inhibiting agent, and may be administered simultaneously, separately or sequentially, with a conventional therapeutic agent, and it may be administered singly or multiply. It is important to administer an amount capable of obtaining the maximum effect with a minimum amount without side effects in consideration to all the factors, and this may be easily determined by those skilled in the art.

According to one example, the pharmaceutically effective dose of the present invention may differ according to the patient's age, gender, condition, body weight, absorption degree of active components in the body, inactivity rate, excretion rate, disease kind, and drug used in combination, and it may be increased or decreased according to the administration route, severity of obesity, gender, body weight, age, and the like, and for example, as an active ingredient, the composition according to one example may be administered so that the MCT inhibitor compound (for example, α-CHC, AZD-3965, and/or SR13800) is 0.0001 μg/kg to 1000 mg/kg, 0.01 μg/kg to 500 mg/kg, 0.1 μg/kg to 100 mg/kg, 1 μg/kg to 90 mg/kg, 10 μg/kg to 80 mg/kg, 100 μg/kg to 70 mg/kg, 1 mg/kg to 60 mg/kg, or 10 mg/kg to 50 mg/kg. In one example, specifically, in case of α-CHC, the composition (MCT inhibitor) according to one example may be administered in eyes at a concentration of 1 mM to 3 mM in an amount of 1 μl to 1 μl, and in case of SR13800, the composition (MCT inhibitor) according to one example may be administered in eyes at a concentration of 1 μM to 5 μM in an amount of 1 μl to 1 ml.

According to one example, the composition (MCT inhibitor) may comprise the MCT inhibitor compound (for example, α-CHC, AZD-3965, and/or SR13800) in an amount of 0.001% by weight to 10% by weight. For example, the composition may comprise the MCT inhibitor compound (for example, α-CHC, AZD-3965, and/or SR13800) of 0.001% by weight, 0.01% by weight, 0.1% by weight, 0.5% by weight, 1.0% by weight, 1.5% by weight, 2.0% by weight, 5.0% by weight, or 10% by weight.

One example provides a method of prevention or treatment of an angiogenesis-related ocular disease comprising administering a composition comprising an inhibitor which inhibits expression of an MCT (Monocarboxylate transporter) gene or activity of an MCT protein to a patient.

According to one example, the method of prevention or treatment of an angiogenesis-related ocular disease may further comprise confirming (selecting) a patient in need of prevention and/or treatment of an angiogenesis-related ocular disease, before administering the inhibitor which inhibits expression of the MCT (Monocarboxylate transporter) gene or activity of the MCT protein.

The confirming a patient may confirming a patient who has angiogenesis specifically in choroid tissue of the patient or has angiogenesis specifically in the retinal pigment epithelium (RPE) layer and choroid tissue.

In one example, the confirming a patient may be performed by confirming that VEGF expression is increased in a macrophage isolated from a biological sample collected from the patient, and additionally, it may further comprise confirming whether VEGF expression is not increased in a retinal pigment epithelium cell and/or endothelial cell isolated from the biological sample, and specifically, it may be performed by confirming whether VEGF is increased by lactic acid. In one example, the biological sample may be a cell isolated from RPE-choroid tissue and/or retinal tissue.

The subject to which the method of treatment is applied means a mammal including rat, livestock, and the like, including humans who have or may have an angiogenesis-related ocular disease, but not limited thereto. By administering the pharmaceutical composition comprising an inhibitor which inhibits expression of an MCT (Monocarboxylate transporter) gene or activity of an MCT protein to the subject, the subject may be efficiently treated.

According to one example, the method of prevention or treatment of an angiogenesis-related ocular disease may provide a method of prevention or treatment of an angiogenesis-related ocular disease, comprising administering a pharmaceutically effective dose of an inhibitor which inhibits expression of an MCT (Monocarboxylate transporter) gene or activity of an MCT protein to a patient. The pharmaceutically effective dose is as described above, and the appropriate total daily usage may be determined by treatment within the correct medical judgement range, and it may be administered once or as divided into several times. However, a specific therapeutic effective dose for a specific patient may be applied differently according to various factors including the specific composition, patient's age, body weight, general health condition, gender and diet, administration time, administration route and secretion rate of the composition, treatment period, drug used together with the specific composition or used simultaneously, including whether other agent is used depending on the kind and degree of the reaction to be achieved and case, and similar factors well known in the medical field.

Other example provides an in vitro method for inhibiting VEGF expression and/or secretion in a cell. The cell may be a cell treated with lactic acid.

In one example, the in vitro method may be for inhibiting VEGF expression and/or secretion increased by treatment of the lactic acid.

The cell to which the in vitro method according to one example is applied may be a macrophage, and retinal pigment epithelium cells and/or endothelial cells may be excluded.

In one example, the in vitro method may be for inhibiting VEGF expression and/or secretion in lactic acid-treated cells, and the degree of inhibition may be the same and/or similar (or statistically insignificant) to lactic acid-untreated cells, and may be such that VEGF expression and/or secretion.

Effects of the Invention

The pharmaceutical composition for preventing or treating an angiogenesis-related ocular disease comprising an MCT expression or activity inhibitor according to one example can effectively prevent or treat an angiogenesis-related ocular disease without affecting the normal function of VEGF required for maintaining homeostasis of choriocapillary and visual cells, by specifically inhibiting only VEGF secreted by infiltrated macrophages, different from conventional treatment.

EXAMPLES

Hereafter, the present invention will be described in detail by examples.

The following examples are intended merely to illustrate the invention and are not construed to restrict the invention.

Referential Example 1. Cells and Reagents

Human APRE-19 cells were obtained from ATCC (Manassas, Va., USA), and were cultured in DMEM (Dulbecco's modified Eagle's medium)/F12 medium (1:1, USA) supplemented by 10% bovine fetal serum (FBS) (Gibco, Carlsbad, Calif.), 1% penicillin-streptomycin (Gibco) and 2 mM L-glutamine (Gibco) in a wet incubator under the conditions of 37° C., 5% $CO_2$. For ARPE-19 monolayer culture, ARPE-19 cells were inoculated in a 24-well tissue culture plate (1.53105 cells per well; Corning, Corning, N.Y., USA) and were maintained in DMEM/F12 medium in which serum was reduced (1% FBS). Confluent monolayer culture having TER (Transepithelial resistance) of 40 Ωcm2 or more was used in the experiment.

HUVEC (Human umbilical vein endothelial cell; Lonza Ltd., Basel, Switzerland) was cultured in EGM-2 (endothelial growth medium-2; Lonza). A human acute monocytic leukemia THP-1 cell line was maintained in RPMI medium containing 10% FBS (Gibco). 15 ng/ml PMA (Sigma-Aldrich Corp., St. Louis, Mo., USA) and THP-1 cells were cultured under the conditions of 37° C., 5% CO2 for 2 days, and the THP-1 cells were differentiated into macrophages.

The confluent ARPE-19 monolayer cells maintained in the 24-well plate were incubated with 10 mM L(+)-lactic acid (Sigma-Aldrich Corp.) under presence or absence of α-CHC (α-cyano-4-hydroxycinnamic acid; Sigma-Aldrich) which was an MCT inhibitor (monocarboxylate transporter inhibitor) of 3 mM for a specified period. HUVEC was inoculated to a 24-well plate at a density of $1×10^5$/well, and when cells reached 60% to 70% confluence, cells were exposed to 10 mM L(+)-lactic acid under presence or absence of 3 mM α-CHC. The THP-1 cells were inoculated in a 24-well plate at a density of $3)(10^5$/well, and they were differentiated into macrophages by PMA treatment, and then were cultured with 20 mM L(+)-lactic acid under presence or absence of 3 mM α-CHC.

In addition, the THP-1 cells were inoculated to a 24-well plate at a density of $3)(10^5$/well, and were differentiated into macrophages by PMA treatment, and then were cultured with 20 mM L(+)-lactic acid, by treating SR13800 (Tocris Bioscience, Bristol, UK) at a concentration of 0.5 to 2 μM and AR-C155858 at a concentration of 300 to 500 nM, respectively, thereto.

Referential Example 2. Choroidal Neovascularization (CNV)-Induced Mouse Production Female wild type C57BL/6J mice aged 7 to 8 weeks (Samtako Co., Gyeonggi, Korea) were used in the experiment. The research protocol was approved by Seoul National University Animal Care and Use Committee (approval number SNU-160114-1), and in all the animal experiment, ARVO (Association for Research in Vision and Ophthalmology) guidelines for Use of Animals in Ocular and Vision Research were followed.

Female C57BL/6J mice aged 7 to 8 weeks were anesthetized by intraperitoneally injecting a mixture of Ketamine 100 mg/kg and Xylazine 10 mg/kg, and by dropping 1% tropicamide (Alcon Laboratories Inc., Fort Worth, Tex., USA) in eyes, the pupils of the mice were expanded. Laser was irradiated in a direction of 3, 6, 9 and 12 o'clock direction of the 2 disc diameter in an optic disc by 831-nm 106 diode laser photocoagulation method (75 μm spot size, 0.1 sec duration time, 120 mW). Bubbling or pop sensing by laser photocoagulation was considered a successful rupture of the Bruch membrane.

To evaluate the anti-angiogenic effect by blocking lactic acid intake in macrophages, on day 1 after laser irradiation, when the macrophages began to infiltrate the laser irradiation site (image area), 3 mM α-CHC 2 μl or PBS (vehicle) 2 μl dissolved in PBS was intravitreally injected, and it was used in the following experiment.

Referential Example 3. Diabetic Retinopathy-Induced Mouse Production

To prepare a diabetic retinopathy model, male wild type C57BL/6J mice aged 7 to 8 weeks were used in the experiment. The research protocol was approved by Seoul National University Animal Care and Use Committee (approval number SNU-190313-1-1).

After administering STZ (streptozotocin, Sigma) to the peritoneal cavity of male C57BL6/J mice aged 7 to 8 weeks, whether high blood glucose was induced was confirmed by measuring blood glucose in 2 days. Mice of which blood glucose was induced to 400 mg/dL or more were selected, and used in the following experiment. From about 10 weeks after administering STZ, diabetic retinopathy began to appear.

At about day 140 after administrating STZ to the diabetic retinopathy-induced mice, 3 mM a-CHC 2 μl dissolved in PBS, 2 μM SR13800 2 μl dissolved in PBS, or PBS (vehicle) 20 μl was intravitreally injected and it was used in the following experiment.

Referential Example 4. Metabolite Extraction and Lactic Acid Concentration Measurement RPE-choroid and/or retinal tissue were isolated from mice, and metabolites were extracted by the aforementioned method (Zhu D et al., Curr Eye Res. 2012; 37:1025-1029.). Specifically, newly isolated tissue was homogenized in 1M PCA (perchloric acid) solution 100 μl, and incubated on ice for 30 minutes and then centrifuged at 15,871 g for 15 minutes. The supernatant was isolated, and 2M KOH (0.25 μl per 1 μl PCA) was added to the supernatant and PCA was neutralized. After centrifuging at 15,871 g for 15 minutes, the isolated supernatant was used for measurement of lactic acid. The concentration of the lactic acid was measured using Lactate Colorimetric/Fluorometric Assay Kit (BioVision, Milpitas, Calif., USA) according to the manufacturer's instructions.

Referential Example 5. Enzyme-Linked Immunosorbent Assay

Cells were treated with lactic acid for 24 hours. The medium was collected and centrifuged at 587 g for 5 minutes and particles were removed and stored at −80° C. before performing ELISA.

The retina and RPE-choroid tissue were isolated from the control (naive; normal group in which CNV was not induced) CNV mouse (on day 3 after laser irradiation) or diabetic retinopathy mouse (on week 20 after STZ administration), and the isolated tissue was homogenized in ice-cold RIPA lysis buffer (Thermo Scientific, Rockford, Ill., USA) containing 1% protease inhibiting cocktail and 1% phosphatase inhibiting cocktail (GenDEPOT, Katy, Tex., USA). After centrifuging at 15,871 g for 15 minutes, the isolated supernatant was used for ELISA analysis. Secretion of VEGF was measured using ELISA Duoset system (R & D Systems, Minneapolis, Minn., USA) according to the manufacturer's instructions.

Referential Example 6. RNA Isolation and Real-Time PCR

Total RNA was extracted in cells using trizole (Invitrogen, Carlsbad, Calif., USA) according to the manufacturer's instructions. RNA concentration/quality was evaluated using a nanodrop spectrophotometer (NanoDrop Technology, Wilmington, Del., USA). An equal amount of RNA was under reverse transcription to cDNA using a reverse transcription kit (Enzynomics, Daejeon, Korea), and quantitative real-time PCR (ABI PRISM 7900, Applied Biosystems) was performed using SYBR Green PCR Master Mix (Applied Biosystems, Foster City, Calif., USA) to measure gene expression. In 12 minutes at 95° C., a cycle consisting of 10 seconds at 95° C. and 30 seconds at 60° C. was performed 50 times.

Relative mRNA expression of each sample was standardized by β-actin and RPL37A, and statistics were analyzed using Student's unpaired t-test. The sequences of primers used for amplification were disclosed in the following Table 1.

TABLE 1

| primer | | Nucleic acid sequence(5'->3') | SEQ ID NO |
|---|---|---|---|
| β-actin | Forward | 5'-ATTGCCGACAGGATGCAGAA-3' | SEQ ID NO: 1 |
| | Reverse | 5'-GCTGATCCACATCTGCTGGAA-3' | SEQ ID NO: 2 |
| RPL37A | Forward | 5'-ATTGAAATCAGCCAGCACGC-3' | SEQ ID NO: 3 |
| | Reverse | 5'-AGGAACCACAGTGCCAGATCC-3' | SEQ ID NO: 4 |
| VEGFA | Forward | 5'-ATTGAAATCAGCCAGCACGC-3' | SEQ ID NO: 5 |
| | Reverse | 5'-AGGAACCACAGTGCCAGATCC-3' | SEQ ID NO: 6 |

Referential Example 7. Immunohistochemistry

THP-1 cells differentiated into macrophages by treating 15 ng/ml PMA for 48 hours were treated with lactic acid for 18 hours and fixed in 4% paraformaldehyde for 15 minutes. Cells were blocked in 5% FBS in PBS containing 0.3% Triton X-100 for 1 hour, and then cultured with the following primary antibody at 48° C. overnight: FITC-conjugated CD68 (KP1; Santa Cruz Biotechnology, Inc., Santa Cruz, Calif., USA) and APC-conjugated anti-mouse-VEGF (C-1, Santa Cruz Biotechnology, Inc.) cells were rinsed and washed with PBS three times. To stain nuclei, cells were treated with nucleus dye DAPI (4',6-diamidino-2-phenylindole) 3 μl for 15 minutes. Stained cells were observed using Olympus FV1000 Confocal Scanning Scope (Olympus, Tokyo, Japan). VEGF intensity was measured using ImageJ software (http://imagej.nih.gov/ij/; provided in the public domain by the National Institutes of Health, Bethesda, Md., USA).

Laser was irradiated to mice by the method of Referential example 2, and on day 3, eyes were extracted from mice, and fixed in 4% paraformaldehyde for 1 hour. After removing the retina, the RPE-choroid tissue was cultured with rat anti-mouse F4/80 (Bio-Rad, Richmond, Calif., USA) and APC conjugated anti-mouse VEGF (C-1; Santa Cruz Biotechnology, Inc.) at 48° C. overnight. A flat mount was washed with PBS for 10 minutes 10 times using an orbital shaker at a room temperature, and then incubated with Alexa-Fluor 488-labeled goat anti-rat IgG (Molecular Probes, Eugene, Oreg., USA) for 1 hour. The stained tissue was examined under Olympus FV1000 Confocal Scanning Scope. The regions of infiltrated macrophages and secreted VEGF were measured using ImageJ software.

Eyes of mice in which diabetes was induced by STZ, prepared by the method of Referential example 3 were extracted and fixed in 4% paraformaldehyde for 1 hour. The anterior segment was removed, and then the retinal tissue was cultured with FITC-conjugated isolectin B4 (Sigma) at 4° C. overnight. After washing with PBS for 10 minutes 10 times using an orbital shaker at a room temperature, the stained tissue was examined under Olympus FV1000 Confocal Scanning Scope.

Referential Example 8. Histology

To confirm the histological shape in eyes, tissue staining was performed. Specifically, eyes (globes) fixed after laser irradiation were embedded in paraffin, and standard hematoxylin and eosin (H&E) staining was performed. The stained parts were digitalized using an optical microscope (Labophot; Nikon, Tokyo, Japan).

Referential Example 9. Quantification of Choroidal Neovascularization (CNV)

For evaluation of CNV, on day 1 after laser irradiation, PBS or α-CHC was injected in eyes, and in 6 days (on day 7 after laser irradiation), the RPE-choroid tissue isolated from the eyes of CNV mice was immunohistologically stained with Alexa-Fluor 594-conjugated IB4 (isolectin B4) (Molecular Probes) to visualize CNV. Images obtained by Olympus FV1000 Confocal Scanning Scope were treated in IMARIS imaging software (Bitplane, Zurich, Switzerland) to quantify the IB4-positive CNV amount.

Referential Example 10. Tube Formation Assay

Matrigel (Corning) with reduced growth factors was thawed at 4° C. overnight. Each well of the 24-well plate cooled in advance was coated with 1000 Matrigel and incubated at 37° C. for 40 minutes. HUVEC (3×104 cells) was suspended in EGM-2 medium of 100 μl, and aliquoted in a macrophage conditioned medium of 400 μl, and cultured under the condition of 37° C., 5% $CO_2$ for 12 hours. The macrophage conditioned medium means that 20 mM lactic acid is treated for 24 hours by stimulating macrophages (or macrophages pretreated for 1 hour with α-CHC) and the medium was replaced and then the supernatant was collected.

Endothelial cell tube formation was visualized by Calcein AM (Corning) and then imaging was conducted using Leica CTR6000 fluorescence microscope (Wetzlar, Germany). The number of the capillary-like structure was quantified by manual counting of low-power field (×10). For each well, 5 independent fields were evaluated, and the mean branch number per field (magnification, ×10) was measured.

Referential Example 11. Flow Cytometry

THP-1 cells which differentiated into macrophages by treating with 15 ng/ml, PMA for 48 hours were treated with lactic acid for 18 hours. Cells which were fixed and its permeability was increased were stained with APC conjugated anti-mouse VEGF (C-1; Santa Cruz Biotechnology, Inc.). The labeled cells were analyzed using LSR-II cytometer (BD Biosciences, San Jose, Calif., USA) and data were analyzed using FlowJo software (version 7.6.2, Ashland, Oreg., USA).

After laser irradiation, on day 1, 3, 7, 14 and 21, laser-irradiated eyes were extracted. After removing the anterior segment and vitreous humor, the posterior segment comprising the retina and RPE-choroid was enzymatically dissociated for 1 hour by treating 1 mg/μl I type collagenase (Sigma-Aldrich Corp.) under the presence of 50 unit/μl DNase I (Sigma-Aldrich Corp.) and decomposed into single cells. After washing the single cell suspension in PBS by centrifuging at 685 g for 5 minutes, the cell pellet was suspended with 200 μl FACS buffer containing 1% BSA and 0.1% sodium azide. For surface staining, the following antibodies were used.: Q655-conjugated anti-mouse CD45 (clone: 30-F11; eBioscience, San Diego, Calif., USA), PE-conjugated anti-mouse F4/80 (clone: BM8; eBioscience), APC eFluor 780-comjugate anti-mouse CD11b (clone: M1/70, eBioscience), V450-conjugated anti-mouse Gr-1 (clone: RB6-8C5; eBioscience), FITC-conjugated anti-rat CD206 (clone: MR5D3, AbD Serotec, Raleigh, N.C., USA).

To detect cytokines in cells, cells were fixed with 1% paraformaldehyde for 15 minutes, and incubated with BD Perm/Wash buffer (BD Pharmingen, San Diego, Calif., USA) for 15 minutes to increase the permeability, and then incubated with an antibody of APC-conjugated anti-mouse VEGF (C-1, Santa Cruz Biotechnology, Inc.) to conduct flat mount immunohistological staining.

Cells labeled using LSR-II cytometer (BD Biosciences, San Jose, Calif., USA) were analyzed and data were analyzed using FlowJo software (version 7.6.2, Ashland, Oreg., USA).

Referential Example 12. Statistical Analysis

All results were expressed as mean±standard error of the mean (SEM). The statistical significance between groups was evaluated by Student's unpaired t-test (two-tailed). $P<0.05$ was considered statistically significant.

Example 1. Lactic Acid Concentration in Choroidal Neovascularization (CNV) Mice

As the method of Referential examples 2 and 8, CNV was induced in mice by laser irradiation, and the control group in which laser was not irradiated and the retinal tissue after laser irradiation were under H&E staining, and it was shown in FIG. 1. In FIG. 1, the left panel represents the retinal tissue of the control group in which laser was not irradiated, and the right panel represents the retinal tissue on day 1 after laser irradiation. When compared with the control group in which laser was not irradiated, on day 1 after laser irradiation, cracks were confirmed in the RPE layer and Bruch membrane. From that, it could be seen that CNV was successively induced in mice by the method of Referential example 2. The CNV mouse model in which choroidal neovascularization was artificially induced by irradiating laser to the retinal epithelial cells of mice and Bruch membrane has been used as an animal model representing choroidal neovascularization and/or age-related macular degeneration.

FIG. 2 is a schematic diagram showing the process of measuring the concentration of lactic acid in the RPE-choroid tissue of CNV mice. As the method of Referential example 3, the RPE-choroid tissue was isolated from CNV mice and metabolites were extracted, and then the concentration of lactic acid was measured. FIG. 3 shows the concentration of lactic acid (mM) in the control group (naive) and RPE-choroid tissue isolated from CNV mice. As shown in FIG. 3, the lactic acid level measured on day 3 (3d) after inducing CNV by laser irradiation was significantly increased compared to the control group in which laser was not irradiated.

Example 2. Effect of Lactic Acid and MCT Inhibitors on VEGF Secretion In Vitro

In the present example, it was tried to investigate how lactic acid affects VEGF secretion according to cell type. To investigate the effect of lactic acid on VEGF expression in the retinal pigment epithelial cells, endothelial cells and infiltrated macrophages, using ARPE-19, HUVEC and PMA-differentiated TPHP-1 macrophages, an in vitro cell experiment was performed. As Referential example 1, each cell was treated with lactic acid.

In ARPE-19, HUVEC and THP-1, VEGFA mRNA and VEGF protein expression was measured by real-time RT-PCR (Referential example 5) and ELISA (Referential example 4), respectively, and the result was shown in FIG. 4a to FIG. 4c. As shown in FIG. 4a and FIG. 4b, the gene transcriptome and protein expression for VEGF in ARPE-19 and HUVEC after treatment of lactic acid did not change significantly, compared to the control group in which lactic acid was not treated (control).

However, as shown in FIG. 4c, in THP-1 macrophages differentiated into PMA, lactic acid significantly increased VEGFA mRNA and protein expression, and after treatment of lactic acid, it increased VEGF expression 3 times or more.

FIG. 5 shows VEGFA mRNA and VEGF protein expression when treating lactic acid to THP-1 cells under presence or absence of the MCT inhibitor (α-CHC). VEGF secretion was increased in THP-1 macrophages about 5 times for 24 hours after stimulating with lactic acid, and when treating the MCT inhibitor (α-CHC) and lactic acid, VEGF secretion (VEGF expression) was reduced, compared to the group in which only lactic acid was treated, and this result was dependent on the concentration of the MCT inhibitor. THP-1 macrophages exposed to the medium acidified to pH 4.5 by HCl did not show significant changes on VEGF expression, and this means that the increase of expression of VEGF by lactic acid is not due to acidification of the culture medium.

FIG. 9a shows the VEGF protein expression when treating lactic acid to THP-1 cells under presence or absence of the MCT inhibitor (SR13800), and FIG. 9b shows the VEGF protein expression when treating lactic acid to THP-1 cells under presence or absence of the MCT inhibitor (AR-C155858). VEGF secretion was significantly increased in THP-1 macrophages for 24 hours after stimulating with lactic acid, and when treating the MCT inhibitor (SR13800) and lactic acid, VEGF secretion was reduced, compared to the group in which only lactic acid was treated, and this result was dependent on the concentration of the MCT inhibitor, but in case of AR-C155858 treatment, VEGF expression increased by lactic acid does not show significant changes.

Example 3. Effect of Lactic Acid on Angiogenesis

To confirm whether macrophages stimulated with lactic acid promote angiogenesis, as the method of Referential example 10, tube formation assay was performed in HUVEC. FIG. 6a and FIG. 6b show the result of the tube formation assay showing whether macrophages stimulated with lactic acid promote angiogenesis in HUVEC under presence or absence of the MCT inhibitor (α-CHC). Specifically, FIG. 6a shows the image of visualizing tube formation of endothelial cells by Calcein AM, and FIG. 6b shows the result of calculating the total branch number using Image J software.

As shown in FIG. 6a, tube formation was significantly increased in endothelial cells (HUVEC) in which supernatant of macrophages stimulated with lactic acid was added, but tube formation increased in endothelial cells (HUVEC) when adding the supernatant collected after treating macrophages pretreated with the MCT inhibitor (α-CHC) with lactic acid was reduced. As shown in FIG. 6b, the number of branches formed when the supernatant of macrophages stimulated with lactic acid was added was increased about 5 times compared to the control group (lactic acid untreated group), and the number of branches was significantly reduced when the supernatant collected after treating macrophages pretreated with the MCT inhibitor (α-CHC) with lactic acid was added, compared to the group in which only lactic acid was treated.

From that, it can be seen that lactic acid induces angiogenesis in endothelial cells and the MCT inhibitor inhibits angiogenesis induced by lactic acid.

Example 4. Infiltration of Macrophages and VEGF Expression in CNV Mice

To investigate the effect of lactic acid in vivo, as the method of Referential example 11, flow cytometry was performed to measure infiltration of macrophages to CNV lesions and VEGF expression.

FIG. 7a to FIG. 7d show the result of performing flow cytometry to investigate infiltration of macrophages into CNV lesions and VEGF expression. Specifically, FIG. 7a shows the result of performing flow cytometry for macrophage markers using cells isolated from the RPE-choroid tissue of CNV mice, and FIG. 7b shows the percentage (%) of macrophages infiltrated in eyes of CNV mice over time after laser irradiation, and FIG. 7c shows a representative histogram for VEGF in macrophages of CNV mice on day 3 after laser irradiation, and FIG. 7d shows the result of quantifying the fluorescence intensity (MFI; mean fluorescence intensity) of VEGF in the control group (naive) and macrophages of CNV mice.

As shown in FIG. 7a and FIG. 7b, from day 1 after laser irradiation, the ratio of macrophages (CD45+CD11b+Gr1-F4/80+) was significantly increased, and the maximum value was shown on day 3, and the ratio of macrophages was increased about 10 times, compared to the control group in which laser was not irradiated. As shown in FIG. 7c and FIG. 7d, on day 3 after laser treatment, the VEGF content in the cells per macrophage of CNV mice was significantly increased, compared to the control group in which laser was not irradiated (naive).

Example 5. Effect of MCT Inhibitors on Angiogenesis in CNV Mice

On day 1 after laser irradiation, PBS (hereinafter, vehicle group) or α-CHC dissolved in PBS (hereinafter, MCT inhibitor-injected group) was intravitreally injected into CNV mice prepared by the method of Referential example 2 to evaluate the effect of MCT inhibitors on angiogenesis in an animal model.

For the vehicle group and MCT inhibitor-injected group, as the method of Referential example 10, flow cytometry was performed to measure the effect of MCT inhibitors on VEGF expression. FIG. 8a and FIG. 8b show the result of performing flow cytometry for VEGF after intravitreally injecting MCT inhibitors into CNV mice. Specifically, FIG. 8a shows a histogram, and FIG. 8b shows the concentration of VEGF by the relative mean fluorescence intensity compared to the staining control group. As shown in FIG. 8a and FIG. 8b, when the MCT inhibitor, α-CHC was injected into CNV mice, VEGF expression was significantly reduced, compared to the vehicle group, and this was similar to that of the control group in which CNV was not induced (naive).

As the method of Referential example 7, in CNV mice on day 3 after laser irradiation, an immunohistochemical experiment was performed to investigate how the MCT inhibitor affected VEGF secretion in infiltrated macrophages. FIG. 8c and FIG. 8d show the result of performing immunohistological staining for F4/80 or VEGF on day 3 after injecting the MCT inhibitor or PBS into CNV mice. Specifically, FIG. 8c is an image obtained by performing immunohistological staining for F4/80 or VEGF in the MCT inhibitor-injected group or vehicle group, and FIG. 8d shows quantified stained parts of F4/80 (left graph) and VEGF (right graph), respectively, using Image J software. As shown in FIGS. 8c and 8d, in the MCT inhibitor-injected group (383,738±196,716 μm2) compared to the vehicle group (523,378±165,071 μm2), the VEGF positive region was significantly reduced in the F4/80 stained macrophage region. However, there was no significant difference in the area of infiltrated macrophages in the vehicle group and MCT inhibitor-injected group. From that, it can be seen that infiltration of macrophages occurs by CNV induction, and the MCT inhibitor effectively inhibits VEGF secretion in infiltrated macrophages.

By the method of Referential example 5, ELISA was performed and the VEGF protein expression was measured in the RPE/choroid (left graph) and retina region (right graph) of the vehicle group and MCT inhibitor-injected group, and this was shown in FIG. 8e. The VEGF protein was increased in the RPE/choroid tissue by CNV induction (2120.5±286.4 pg/tissue g), and the amount of the VEGF protein increased by CNV induction was significantly reduced in the MCT inhibitor-injected group.

The result of quantifying CNV by performing immunohistological staining for IB4 in the RPE-choroid tissue isolated from the vehicle group and MCT inhibitor-injected group on day 7 after laser irradiation by the method of Referential example 9 was shown in FIG. 8f and FIG. 8g. FIG. 8f is a confocal image obtained by performing immunohistological staining for IB4 (isolectin B4) in the vehicle group (top image) and MCT inhibitor-injected group (bottom image), and FIG. 8g shows a graph of quantifying IB4 positive signals. In FIG. 8f, the red dotted line represents regions stained with IB4. As shown in FIG. 8f and FIG. 8g, IB4-positive endothelial cells were significantly reduced in the MCT inhibitor-injected group (74,160.6±12,339.5 $\mu m^3$) compared to the vehicle group (141,472.9±49,186 $\mu m^3$).

As shown in FIG. 8f, it could be seen that CNV was induced successfully in mice by the method of Referential example 2, and when intravitreally injecting the MCT inhibitor, choroid vascularization was inhibited.

Overall, from the above result, it could be seen that VEGF secretion was significantly reduced and abnormal angiogenesis by infiltrated macrophages was effectively inhibited, as the MCT inhibitor blocked transport of lactic acid in macrophages in the CNV animal model.

Example 6. Effect of MCT Inhibitors in Diabetic Retinopathy-Induced Mice

Example 6-1. Concentration of Lactic Acid in Diabetic Retinopathy-Induced Mice The lactic acid concentration was evaluated using the method of Referential example 4 in eyes (retina and RPE-choroid tissue) of 1-year diabetes-induced obese mice (hereinafter, db/db mice, diabetic retinopathy was induced enough). FIG. 10a is a schematic diagram showing the process of measuring the concentration of lactic acid in the retina and RPE-choroid tissue of db/db mice. FIG. 10b shows the lactic acid concentration (mM) in the control group (wild-type) and the retina and RPE-choroid tissue isolated from db/db mice. As shown in FIG. 10b, the level of lactic acid in the retina tissue was significantly increased by induction of diabetes, compared to the control group, but significant changes were not observed in the level of lactic acid in the RPE-choroid tissue.

Example 6-2. Measurement of Blood Glucose in Diabetic Retinopathy-Induced Mice As the method of Referential example 3, mice in which diabetes was induced by STZ were produced and the increase of blood glucose was evaluated. FIG. 11a is a schematic diagram showing the process of preparing mice in which diabetic retinopathy (DR) was induced. FIG. 11b shows the result (mg/dL) of measuring blood glucose in blood of wild type mice (WT) and mice in which diabetes and diabetic retinopathy were induced by STZ (STZ). As shown in FIG. 11a, the blood glucose was significantly increased by intraperitoneal injection of STZ.

Example 6-3. Measurement of VEGF Expression in Diabetic Retinopathy-Induced Mice In the present example, as the method of Referential examples 3 and 4, PBS (hereinafter, vehicle group) or α-CHC and SR13800 dissolved in PBS were intravitreally injected, respectively, into eyes of diabetes and diabetic retinopathy-induced mice to evaluate the effect of α-CHC and SR13800 on angiogenesis in the diabetic retinopathy animal model. FIG. 12 shows a graph of measuring the VEGF protein secretion (expression) (ng/tissue g) of the retina and RPE-choroid tissue in the vehicle group and α-CHC administration group. FIG. 13 shows a graph of measuring the VEGF protein expression of the retina and RPE-choroid tissue by intraocular injection of the vehicle group and SR13800 administration group.

As shown in FIG. 12 and FIG. 13, in the RPE-choroid tissue, VEGF expression was not significantly increased by STZ administration (by induction of diabetic retinopathy), but in the retinal tissue, VEGF expression was significantly increased by STZ administration, and in particular, in the SR13800 administration group, the VEGF expression increased in the retinal tissue by induction of diabetic retinopathy was significantly reduced, and SR13800 administration did not affect VEGF expression in the RPE-choroid tissue at all.

Example 6-4. Confirmation of Angiogenesis in Retina of Diabetic Retinopathy-Induced Mice By the method of Referential example 3, PBS (hereinafter, vehicle group) or α-CHC and SR13800 dissolved in PBS were intravitreally injected, respectively, into eyes of diabetes and diabetic retinopathy-induced mice by STZ to evaluate the effect of the MCT inhibitor on angiogenesis by the tissue staining method as the method of Referential example 7. FIG. 14 is a picture of photographing changes of retinal blood vessel bleeding and angiogenesis of STZ mice by intraocular injection (intravitreal injection) of the vehicle group, α-CHC administration group and SR13800 administration group, and the blood vessel was stained using IB4 (isolectin B4). As shown in FIG. 14, it could be confirmed that α-CHC and SR13800 reduced bleeding and angiogenesis increased in the diabetic retinopathy model by intraocular injection, and in particular, SR13800 significantly reduced bleeding and angiogenesis.

What is claimed is:

1. A method of prevention or treatment of an angiogenesis-related ocular disease,
    comprising administering an inhibitor which inhibits expression of an MCT (Monocarboxylate transporter) gene or activity of an MCT protein to a subject in need of prevention or treatment of the angiogenesis-related ocular disease,
    wherein the inhibitor is SR13800 or αCHC (α-cyano-4-hydroxycinnamate).

2. The method of prevention or treatment of an angiogenesis-related ocular disease according to claim 1, wherein the MCT gene is at least one selected from the group consisting of MCT1, MCT2, MCT3, and MCT4.

3. The method of prevention or treatment of an angiogenesis-related ocular disease according to claim 1, wherein the MCT protein is at least one selected from the group consisting of MCT1, MCT2, MCT3, and MCT4.

4. The method of prevention or treatment of an angiogenesis-related ocular disease according to claim 1, wherein the inhibitor inhibits secretion of VEGF (vascular endothelial growth factor) in macrophages.

5. The method of prevention or treatment of an angiogenesis-related ocular disease according to claim 1, wherein the angiogenesis-related ocular disease is at least one selected from the group consisting of age-related macular degeneration, diabetic retinopathy, diabetic macular edema, choroidal neovascularization, angiogenic glaucoma, corneal angiogenesis, central retinal vein occlusion, branch retinal vein occlusion, proliferative vitreoretinopathy, pigmental retinopathy, ischemic optic neuropathy, retinopathy of prematurity, epidemic keratoconjunctivitis, angiogenic iris disease, retrolental fibroplasia, atopic keratitis, superior limbic keratitis, pterygium, and phlyctenular keratoconjunctivitis.

6. The method of prevention or treatment of an angiogenesis-related ocular disease according to claim 1, wherein the inhibitor is at least one formulation selected from the group consisting of eye drop, eye ointment, injection, eye intercalator, granule, tablet, pill, capsule, gel, syrup, suspension, emulsion, drip, and liquid.

7. The method of prevention or treatment of an angiogenesis-related ocular disease according to claim 1, wherein the administration route of the inhibitor is at least one selected from the group consisting of intravitreal administration, intraconjunctival administration, subconjunctival administration, and subtenon administration.

* * * * *